United States Patent [19]

Hill et al.

[11] Patent Number: 5,507,784
[45] Date of Patent: Apr. 16, 1996

[54] METHOD AND APPARATUS FOR CONTROL OF A-V INTERVAL

[75] Inventors: Michael R. S. Hill, Brooklyn Park; Rahul Mehra, Stillwater, both of Minn.

[73] Assignee: Medtronic, Inc., Minneapolis, Minn.

[21] Appl. No.: 419,068

[22] Filed: Apr. 6, 1995

Related U.S. Application Data

[62] Division of Ser. No. 125,579, Sep. 23, 1993, Pat. No. 5,411,531.

[51] Int. Cl.$^6$ .................................................. A61N 1/362
[52] U.S. Cl. ........................................ 607/14; 607/9
[58] Field of Search ............................ 607/4, 9, 14, 17

[56] References Cited

U.S. PATENT DOCUMENTS

| | | |
|---|---|---|
| 3,937,226 | 2/1976 | Funke . |
| 4,088,140 | 5/1978 | Rockland . |
| 4,354,497 | 10/1982 | Kahn . |
| 4,817,605 | 4/1989 | Sholder . |
| 5,027,815 | 7/1991 | Funke . |
| 5,203,326 | 4/1993 | Collins ........................................ 607/4 |
| 5,273,035 | 12/1993 | Markowitz . |
| 5,356,425 | 10/1994 | Bardy et al. ............................... 607/14 |

OTHER PUBLICATIONS

AHA, 1991, Abstracts from Teh 64th Scientific Sessions #1804 "Simultaneous Dual Atrium Pacing in High Degree Intraarterial Blocks: Hemodynamic Results" Dauber et al.
PACE vol. 14, Apr., 1992, Part II, p. 648, "Prevention of Atrial Tachyarrhythmias Related to Advanced Interarterial Block by Permanent Atrial Resynchronization" Mabo et al., #122.
PACE, vol. 14, Apr. 1991, Part. II, p. 650, "Heomodynamic Benefits of Permanent Atrial Resynchronization in Patients with Advanced Interatial Blocks, Paced in DDD Mode", Daubert et al. #130.
PACE, vol. 15, Apr. 1992, Part II, "Renewal of Permanent Left Atrial Pacing Via the Cornonary Sinus", p. 572. #255.
PACE, vol. 16, Apr., 1993, Part II, p. 885, "Permanent Dual Atrium Pacing in Major Interatrial Conduction Blocks: A Four Years Experience", Daubert et al., #141.
"Does Dual Chamber or Atrial Pacing Prevent Atrial Fibrillation? The Need for a Randomized Controlled Trial", by Lamas et al., in PACE, vol. 15(8), Aug., 1992.
"Validation of Double–Spike Electrograms as Markers of Conduction Delay or Block in Atrial Flutter", by Cosio et al., in The American Journal of Cardiology, Apr. 1, 1988, vol. 61.
"Demonstration of Macroentry and Feasibility of Operative Therapy in teh Common Type of Atrial Flutter", by Klein et al., in Mar. 1, 1986, The American Journal of Cardiology, vol. 57.

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

A device for controlling the duration of A-V conduction intervals ia a patient's heart. Stimulation of the AV nodal fat pad is employed to maintain the durations of the A-V conduction intervals within a desired interval range, which may vary as a function of sensed heart rate or other physiologic parameter. AV nodal fat pad stimulation may also be triggered in response to defined heart rhythms such as a rapid rate or the occurrence of PVC's, to terminate or prevent induction of arrhythmias.

4 Claims, 7 Drawing Sheets

METHOD AND APPARATUS FOR CONTROL OF A-V INTERVAL

This is a divisional of application Ser. No. 08/125,579, filed Sep. 23, 1993, now U.S. Pat. No. 5,411,531.

Cross reference to commonly assigned co-pending applications:

Reference is made to U.S. application Ser. No. 07/906,914 by Bardy et al. for a "Method and Apparatus for treatment of Atrial fibrillation and Flutter", U.S. application Ser. No. 07/906,959 by Bardy for a "Method and Apparatus for Treatment of Angina" and U.S. application Ser. No. 07/906,806 by Mehra for a "Method and Apparatus for Discrimination of Ventricular and Supraventricular Tachycardia", all filed June 30, 1992.

BACKGROUND OF THE INVENTION

This invention relates to implantable stimulators generally and more particularly to implantable nerve stimulators and pacemakers.

It is known that stimulation of the vagus nerve can reduce the sinus rate, as well as prolong the A-V conduction time or, if stimulation energies are high enough, induce A-V block. Use of vagal nerve stimulation to treat supraventricular arrhythmias and angina pectoris is disclosed in the article "Vagal Tuning" by Bilgutay et al., *Journal of Thoracic and Cardiovascular Surgery*, Vol. 56, No. 1, July, 1968, pp. 71–82. It is also known that stimulation of the carotid sinus nerve produces a similar result, as disclosed in the article "Carotid Sinus Nerve Stimulation in the Treatment of Angina Pectoris and Supraventricular Tachycardia" by Braunwald et al., published in California Medicine, Vol. 112, pp. 41–50, March, 1970.

The nervous system regulating the rhythm of the heart also includes a number of highly ganglionated plexi or "fat pads" at various locations on the heart, including fat pads associated with the SA and A-V nodes. The fat pad associated with the SA node is located overlying the right pulmonary vein entrance in dogs, and is located along the anterior AV groove in most humans. The fat pad associated with the AV node is located at the junction of the inferior vena cava and the inferior left atrium in dogs, and is located along the posterior AV groove in most humans.

As set forth in "Functional Anatomy of the Cardiac Efferent Innervation" by Randall et al., in *Neurocardiology*, edited by Kulbertus et al, Futura Publishing Co., 1988, direct surgical excision of the fat pad associated with the SA node affects the functioning of the SA node without significantly affecting the AV node. Similarly, excision of the fat pad associated with the AV node affects functioning of the AV node without significantly affecting the SA node.

As set forth in the article "Parasympathetic Postganglionic Pathways to the Sinoatrial Node", Bluemel et al., *Am. J. Physiol.* 259, (Heart Circ. Physiol. 28) H1504–H1510, 1990, stimulation of the fat pad associated with the SA node results in slowing of the sinus rate without the accompanying prolongation of A-V conduction time which normally results from vagal nerve stimulation. The article also indicates that stimulation of the fat pad associated with the AV node is believed to produce corresponding effects limited to the AV node, i.e., extension of the A-V conduction time without concurrent slowing of the sinus rate.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in *Circulation Research*, Vol. 46, No. 1, January, 1980, pp. 48–57, the fat pads associated with both the AV node and the SA node may be stimulated by means of electrodes located in the right pulmonary artery. The results obtained include both a depression of the sinus rate and a prolongation of the A-V conduction time in response to continuous stimulation at 2–80 Hz at up to 50 ma.

SUMMARY OF THE INVENTION

Cardiac function may be compromised by a variety of factors. For example, the coronary artery disease, hypertensive heart disease or dilated cardiomyopathy may impair the heart's hemodynamics on a chronic basis. In addition, patients suffering from AV junctional disrhythmias, PVC induced atrial fibrillation or those prone to supraventricular tachycardias may suffer from hemodynamic impairment on an intermittent basis. The duration of the A-V interval plays an important role in control of the hemodynamics of the heart. Traditionally, control of the A-V interval has been accomplished by means of drugs or ablation. Drug therapy is typically effective on a chronic basis and does not provide A-V interval control which varies on a physiological basis. Ablation has a very narrow window of available adjustment and is permanent.

The present invention is directed to improving heart hemodynamics by controlling the A-V interval by means of stimulation of the A-V nodal fat pad in a fashion that allows the A-V interval to follow physiologic changes. This desired result is accomplished by means of feedback regulation of the stimulation pulses applied to the AV nodal fat pad, based on their measured effects. The effects of the fat pad stimulus pulses are measured by comparing the observed A-V intervals following burst stimulation with a desired A-V interval or A-V interval range, as indicated by other measured physiologic parameters, such as heart rate. Parameters of the burst stimulus pulses are modified in order to maintain the observed A-V intervals within the desired interval range.

In some patients, control of the A-V interval by burst stimulation may be desirable at all times. In such patients, observed A-V interval durations without burst stimulation which are less than the desired interval range may activate the burst stimulation function. Deactivation of the burst stimulation function may correspondingly occur in response to observed A-V intervals during burst stimulation exceeding the desired interval range.

In patients in whom hemodynamic compromise typically occurs primarily in conjunction with an identifiable heart rhythm, such as a supraventricular tachycardia, occurrence of such a rhythm may be employed as an additional condition precedent for fat pad stimulation. In such embodiments of the present invention, burst stimulation may be activated whenever the specified rhythm occurs, or activated only if the observed A-V intervals during that rhythm fall outside of the desired interval range. Feedback control may be retained to assure appropriate levels of stimulation of the A-V nodal fat pad.

In addition to improving heart hemodynamics while a tachycardia persists, the present invention also inherently functions to address hemodynamic compromise due to the presence of certain tachycardias by terminating them or by preventing their induction. For example, modification of the A-V interval duration by itself may be effective to terminate some non-sinus supraventricular tachycardias, and may assist in avoiding initiation of atrial fibrillation due to retrograde conduction following the occurrence of PVC's.

BRIEF DESCRIPTION OF THE DRAWINGS

The above and still further objects, features and advantages of the present invention will become apparent from the following detailed description, taken in conjunction with the accompanying drawings, and, in which.

DETAILED DESCRIPTION OF THE PREFERRED EMBODIMENTS

Figure 1A:
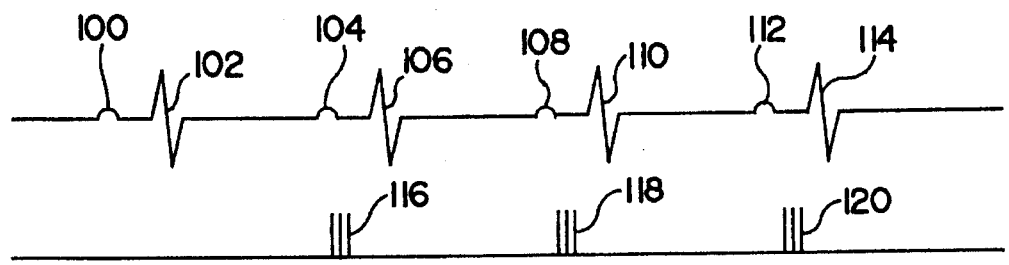
FIGS. 1A–1D include simulated EGM tracings and timing diagrams, illustrating the basic operation of the present invention.

FIGS. 1A through 1D are simulated electrograms and timing diagrams illustrating the operation of a device embodying the present invention. Generally, the present invention provides a burst of one or more pulses intended to stimulate the AV nodal fat pad, delivered synchronized to sensed atrial or ventricular depolarizations. The pulse bursts are not intended to induce depolarizations of the atrium or ventricle, and are delivered during the absolute refractory periods following the occurrence of depolarizations in the chamber to which they are synchronized. Pulse bursts are synchronized to the ventricle if the electrodes used for fat pad stimulation are located such that the burst stimulus pulses may trigger depolarization of the ventricle and are synchronized to the atrium if the electrodes used for fat pad stimulation are located such that the burst stimulus pulses may trigger depolarization of the atrium. In order for the device to function properly, it is necessary that the burst stimulus electrodes be placed in a location in which the burst stimulus pulses will not trigger depolarizations of a heart chamber to which they are not synchronized.

The burst stimulation is delivered in an effort to prolong the A-V conduction interval so that it falls within a desired range. The amplitude pulse width, pulse number or frequency of the pulses in the bursts are controlled as a function of the observed A-V intervals following stimulation, with stimulation intensity increased if the resultant A-V delay is shorter than desired and stimulation intensity decreased if the resultant A-V interval is longer than desired.

In its disclosed embodiment, the invention takes the form of a dual chamber pacemaker which operates in the DDD pacing mode, sensing and pacing in both the atrium and ventricle of the heart. However, the invention may also be practiced in a VDD pacer, a DDI pacer, or in other devices which sense in both the atrium and ventricle, including devices which provide other therapeutic functions such as anti-tachycardia pacing, cardioversion or defibrillation.

The disclosed pacemaker defines a desired range of A-V interval durations which vary as a function of sensed heart rate. However, variation of the desired A-V interval range may also be accomplished as a function of a different measured parameter, such as physical activity, mixed venous oxygen saturation, right ventricular pressure, and so forth, particularly if such sensed parameters are also employed to control the basic pacing rate of the pacemaker. In order to facilitate sensing the duration of the A-V intervals resulting following fat pad stimulation, the pacer sets its own A-V escape interval (the interval separating atrial depolarizations and corresponding synchronized ventricular pacing pulses) to be greater than or equal to the upper endpoint of the desired range of A-V intervals.

The burst stimulation function may be continuously or intermittently enabled. If continuously enabled, burst stimulation is activated in response to the observed A-V interval, absent burst stimulation, falling below the lower endpoint of the desired interval range, with stimulus pulse parameters adjusted thereafter to maintain the A-V interval within the desired range. Alternatively the burst stimulation function may be enabled only intermittently in response to the occurrence of a defined heart rhythm, e.g., high ventricular rate or premature ventricular depolarizations (PVC's). In the case of enablement due to high ventricular rate, burst stimulation may activated in response to the observed A-V interval, during the period of high rate, absent burst stimulation, falling below the lower endpoint of the desired interval range. In such case, stimulus pulse parameters may be adjusted thereafter to maintain the A-V interval within the desired range, so long as the rapid rate persists.

In the case of enablement of burst function in response to the occurrence of PVC's, activation need not be dependant on measured A-V intervals, and may occur directly in response to the occurrence of a specified number or distribution of PVC's. In this case, feedback control of stimulus burst parameters based on sensed A-V intervals may be omitted, with burst parameters specified by physician programming.

FIGS. 1A through 1D illustrate the operation of the device as discussed above. In each of these figures, the upper strip is a simulated electrogram and the lower tracing is a timing diagram illustrating the timing and amplitude of synchronized burst stimulation pulses. The burst pulses are not shown on the simulated electrogram. However, it should be understood that the burst pulses would appear on actual electrograms.

FIG. 1A illustrates the operation of a device according to the present invention to provide atrial synchronized AV nodal stimulus bursts. For purposes of FIG. 1A, as well as for purposes of FIGS. 1B, 1C and 1D, at the beginning of the simulated electrograms, it should be assumed that AV nodal fat pad stimulus pulses were not previously being provided, due to the fact that the previous measured A-V intervals, without burst stimulation, fell within the desired interval range. Therefore, the initial parameters of the stimulus pulses are set at nominal initial values, determined by programming.

In FIG. 1A, atrial depolarization (P-wave) 100 is followed by ventricular depolarization (R-wave) 102. The observed A-V conduction interval between them is less than the lower limit of the desired A-V interval range. In response, the device delivers a stimulus burst 116 to the electrodes intended to stimulate the AV nodal fat pad. Stimulus burst 116 is synchronized to sensed P-wave 104, falling within refractory period of the atrium. The full effect of the stimulus pulses may not occur until the second or third heart cycle, or possibly later, following activation of the burst stimulation function. Thus, the device waits until at least a predetermined number (e.g. 3) of heart cycles have occurred following initiation of burst stimulation or adjustment of burst stimulus pulse parameters before attempting to assess the efficacy of the stimulation. Stimulus bursts 118 and 120 have the same pulse parameters as burst 116.

As illustrated, R-wave 106 follows P-wave 104 by an A-V interval which is approximately the same as the A-V interval separating P-wave 100 from R-wave 102, with the A-V interval increasing between P-wave 108 and R-wave 110 and reaching full extension between P-wave 112 and R-wave 114. Because 3 heart cycles have occurred (3 stimulus bursts have been delivered) since activation of the burst stimulus function, the device checks to see if the A-V intervals have increased to a duration within the desired interval range. If so, burst pulse parameters will remain unchanged until the observed A-V intervals move outside the desired range.

Figure 1B:
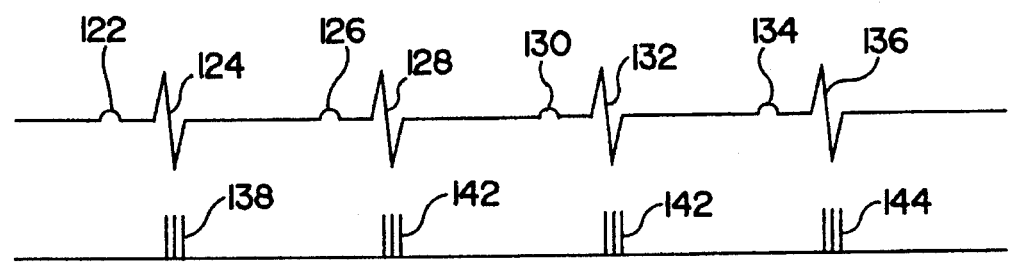

FIG. 1B illustrates the operation of an embodiment of the present invention in which stimulus pulse bursts are synchronized to sensed R-waves. P-wave 122 is separated from R-wave 124 by an A-V interval which is less than the lower limit of the desired A-V interval range. In response, the device delivers a stimulus pulse burst 138 to the electrodes intended to stimulate the A-V nodal fat pad, synchronized to R-wave 124, and falling within the refractory period of the ventricle. The next following A-V interval, separating P-wave 126 and R-wave 128 is somewhat prolonged. The A-V interval separating P-wave 130 and R-wave 132 is further prolonged, and falls within the desired A-V interval range. Thus, parameters of pulse burst 144 remain the same as for pulse bursts 138, 140 and 142. The A-V interval separating P-wave 134 and R-wave 136 similarly falls within the desired A-V interval range, resulting in delivery of the next stimulus pulse burst with the same parameters as pulse burst 144.

Figure 1C:
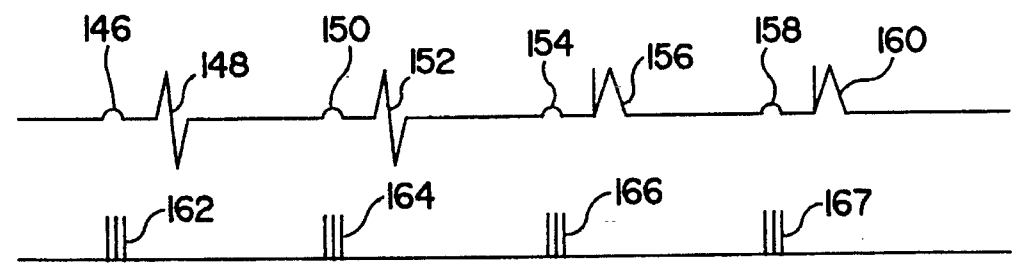

FIG. 1C illustrates the operation of a device according to the present invention in which the initial stimulus pulse burst parameters provide an excessive prolongation of the A-V interval. The A-V interval (not illustrated) prior to P-wave 146 and R-wave 148 was less than the lower limit of the desired A-V interval range, leading to triggering of stimulus pulse burst 162, synchronized to P-wave 148. The A-V interval separating P-wave 150 and R-wave 152 is somewhat prolonged, but the A-V interval separating P-wave 154 and the intrinsic R-wave which would normally follow exceeds the device's A-V escape interval, leading to delivery of a pacing pulse at 156. As discussed above, the A-V escape interval of the pacer is chosen to fall at or outside of the upper end of the desired A-V interval range. As a result, the next stimulus pulse burst 167, synchronized to P-wave 158 is of reduced intensity as compared to stimulus bursts 162, 164 and 166. Reduction of intensity may be accomplished by reducing the number of pulses, frequency, width or amplitude of the pulses. As illustrated, reduction in stimulus intensity is accomplished by the amplitude of the pulses. The resulting observed A-V interval between P-wave 158 and paced R-wave 160 still falls outside the desired A-V interval range, but the device will wait until the third stimulus burst following the parameter adjustment before assessing whether the downward adjustment of stimulus intensity was successful.

Figure 1D:
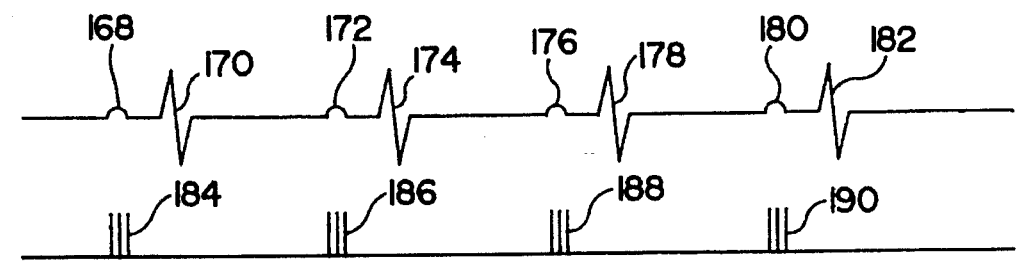

FIG. 1D illustrates the operation of a device according to the present invention in which the initial parameters of the stimulus pulse bursts are inadequate to produce the desired A-V interval prolongation. The A-V interval (not illustrated) prior to P-wave 168 and R-wave 170 was less than the lower limit of the desired A-V interval range, leading to triggering of stimulus pulse burst 184, synchronized to P-wave 168. The A-V interval separating P-wave 172 and R-wave 174 is only slightly prolonged, and the A-V interval separating P-wave 176 and R-wave 178 is still less than the desire A-V interval range. As a result, the next stimulus pulse burst 190, synchronized to P-wave 180, is delivered at an increased stimulation intensity as compared to pulse bursts 184, 186 and 188. As illustrated, the stimulation intensity is increased by increasing the amplitude of the stimulus pulses. However, as noted above, stimulation intensity can be adjusted by increasing the number of pulses, increasing the width of the pulses or adjusting the frequency of the pulses as well. The resulting observed A-V interval between P-wave 180 and R-wave 182 still falls outside the desired A-V interval range, but the device will wait until the third stimulus burst following the parameter adjustment before assessing whether the upward adjustment of stimulus intensity was successful.

Figure 2:
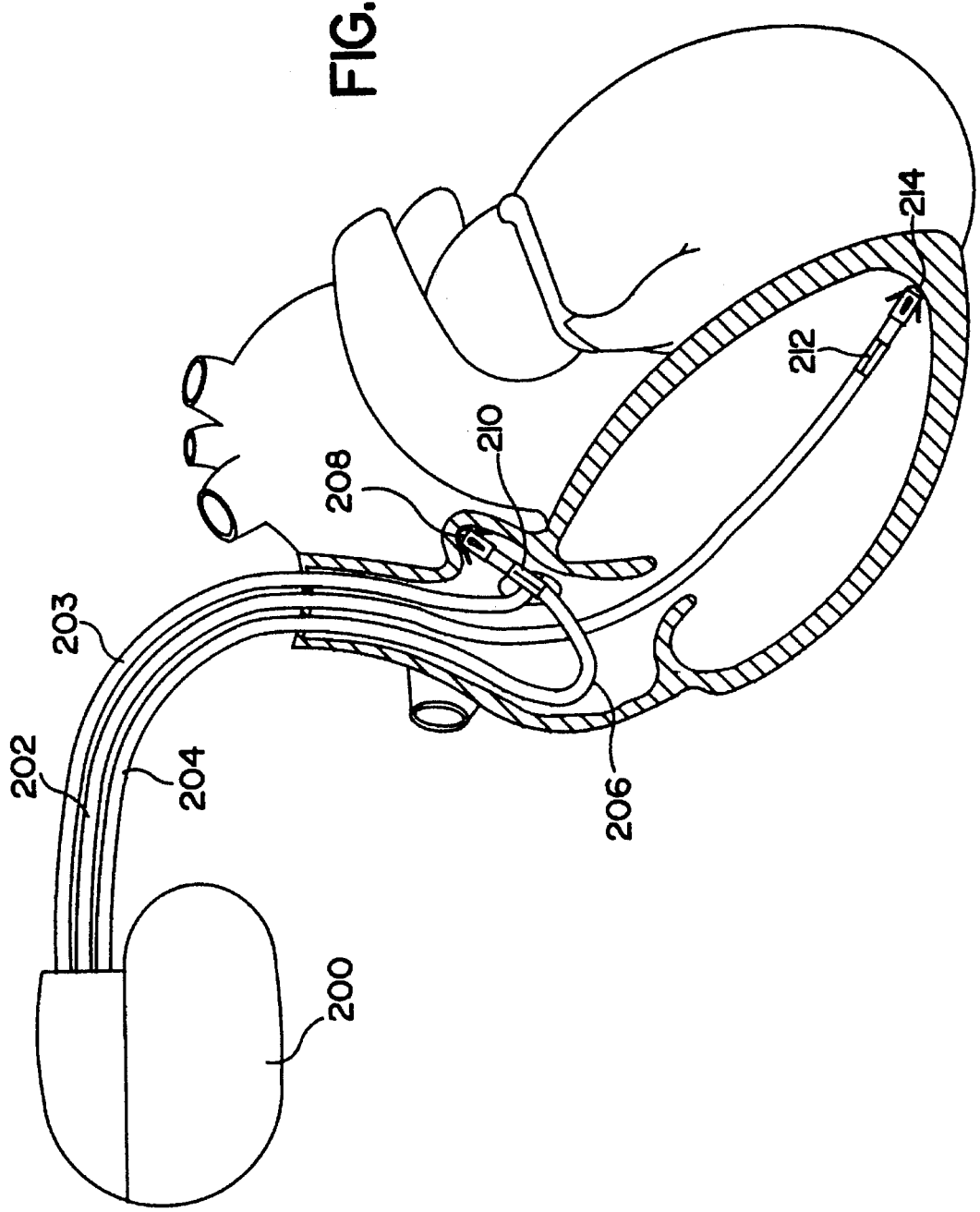
FIG. 2 is an illustration of one embodiment of a combination pacing and fat pad stimulation lead system for use with the present invention.

FIG. 2 is a cutaway view of the heart illustrating an implantable pacemaker/fat pad stimulator and an associated lead system. The combination pacemaker/fat pad stimulator 200 is shown diagrammatically, and is provided with three endocardial leads 202, 203 and 204 which enter the heart through the superior vena cava. Lead 204 is an atrial lead having a J-shaped configuration adapted to locate its distal end in the right atrial appendage, similar to atrial pacing leads presently marketed. Lead 204 is provided with a closely spaced pair of electrodes 208 and 210 which function to sense spontaneous atrial depolarizations and to pace the atrium, if necessary. Lead 202 is provided with two electrodes 212 and 214 adapted for location in the right ventricular apex.

Lead 203 is employed to stimulate the AV nodal fat pad, and is provided with two electrodes (not visible) located within the coronary sinus, adjacent the ostium. In this location, the stimulus bursts are unlikely to trigger depolarizations of the ventricle, but may trigger depolarizations of the atrium, so atrial synchronized burst stimulation should be employed. Electrodes located more deeply in the coronary sinus or great vein, or elsewhere may trigger ventricular depolarizations, requiring ventricular synchronized burst stimulation. AV nodal fat pad stimulation may also be accomplished by means one electrode located adjacent the ostium of the coronary sinus and a second electrode located in the inferior vena cava, by means of electrodes located in the left atrium or by means of epicardial electrodes applied on or adjacent the AV nodal fat pad. The most effective electrode location and the tendency to cause depolarization of heart chambers may vary from patient to patient, and may be determined empirically.

Figure 3:
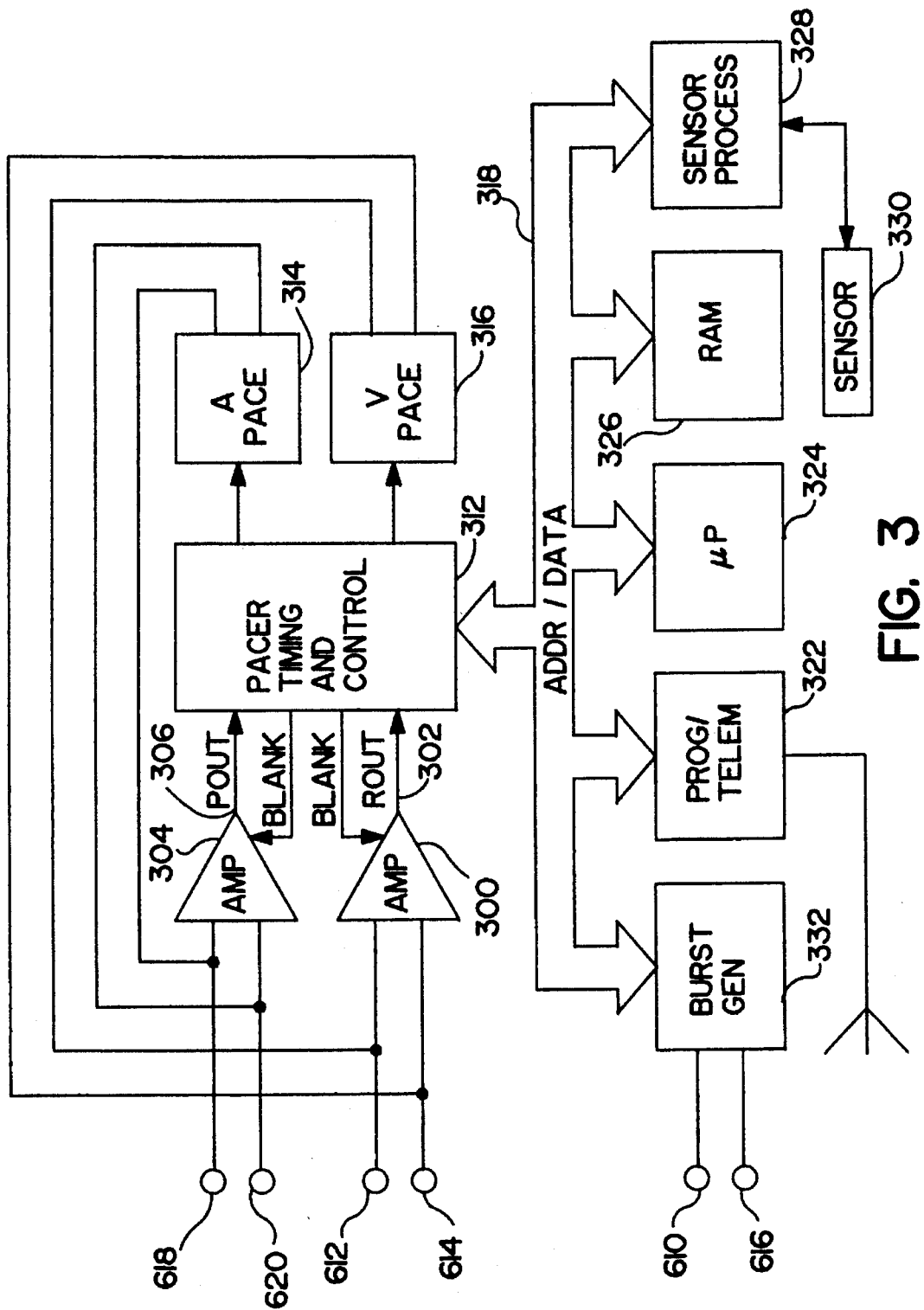
FIG. 3 is a functional block diagram illustrating an implantable pacemaker/fat pad stimulator in which the present invention may be embodied.

FIG. 3 is a functional schematic diagram of an implantable pacemaker/fat pad stimulator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to the implantable pacemakers and/or pacemaker/cardioverter/defibrillators presently commercially sold or being implanted for clinical evaluation in the United States.

The device is provided with an electrode system including electrodes as illustrated in FIG. 2. Electrodes 610 and 616 correspond to the electrodes located on lead 203 (FIG. 2). As discussed, other electrode configurations for AV nodal fat pad stimulation may also be used.

Electrodes 612 and 614 correspond to electrodes 212 and 214 (FIG. 2) and are coupled to the R-wave amplifier 300, which preferably takes the form of a gain controlled amplifier providing an adjustable sensing threshold as a function of the measured R-wave amplitude. A signal is generated on R-out line 302 whenever the signal sensed between electrodes 612 and 614 exceeds the present sensing threshold.

Electrodes 618 and 620 correspond to electrodes 208 and 210 (FIG. 2) and are coupled to the P-wave amplifier 304, which preferably also takes the form of a gain controlled amplifier providing an adjustable sensing threshold. A signal is generated on P-out line 306 whenever the signal sensed between electrodes 618 and 620 exceeds the present sensing threshold.

The band pass characteristics of amplifiers 300 and 304 may be optimized for sensing R-waves and P-waves, respectively. The general operation of the R-wave and P-wave amplifiers 300 and 304 may correspond to any of the numerous such amplifiers presently employed in cardiac pacemakers.

Burst generator 332 may employ any appropriate technology for generation of stimulation pulses in the form of individual pulses or pulse trains, having amplitudes up to 70 ma, pulse widths of up to 0.5 ms, and frequencies of up to 1000 Hz. For example, the Medtronic Model 2349 Programmable Stimulator, as discussed in the above cited Cooper et al. reference includes circuitry for generating appropriate stimulation pulses and trains, although in some cases amplitudes in excess of its 30 ma capability are desirable. For example, the inventors have determined that in dogs, stimulus pulse bursts of 30–50 ma, 0.1—0.3 ms, at 10-100 Hz may be employed, and in humans, pulses of 50 ma, 0.5 ms, at 50 Hz are believed effective. Given that circuitry for pulse burst generation has become well known to those skilled in the art and is commercially available, no detailed disclosure is included herein.

The specific timing, amplitude, duration and number of pulses is controlled by microprocessor 324 via address/data bus 318 under control of the programming stored in random access memory 326. Programming of the device is accomplished by means of telemetry circuit 322, which may correspond to circuitry employed to accomplish this function in prior art pacemakers.

Much of the remainder of the circuitry is dedicated to the provision of cardiac pacing therapies, which for purposes of the present invention may correspond to the prior art. The pacer timing/control circuitry 312 includes programmable digital counters which control the basic time intervals associated with DDD, VDD, DDI or other modes of pacing well known to the art. Circuitry 312 also may optionally also control escape intervals associated with anti-tachyarrhythmia pacing in both the atrium and the ventricle, employing any tachyarrhythmia detection and pacing therapies known to the art.

Intervals defined by pacing circuitry 312 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 324, in response to stored data in memory 326 and are communicated to the pacing circuitry 312 via address/data bus 318. Pacer circuitry 312 also determines the amplitude of the cardiac pacing pulses under control of microprocessor 324.

During pacing, the escape interval counters within pacer timing/control circuitry 312 are reset upon sensing of R-waves and P-waves as indicated by signals on lines 302 and 306, and in accordance with the selected mode of pacing, on timeout trigger generation of pacing pulses by pacer output circuits 314 and 316, which are coupled to electrodes 618, 620, 612, 614. The escape interval counters are also reset on generation of pacing pulses, and thereby control the basic timing of cardiac pacing functions, including anti-tachyarrhythmia pacing. The durations of the intervals defined by the escape interval timers are determined by microprocessor 324, via data/address bus 318. The values of the counts present in the escape interval counters when reset by sensed R-waves and P-waves or delivery of pacing pulses may also be used to measure the durations of V-V intervals, V-A intervals, A-V intervals and A-A intervals.

Microprocessor 324 operates as an interrupt driven device, and is responsive to interrupts from pacer timing/control circuitry 312 corresponding to the occurrence sensed P-waves and R-waves and corresponding to the generation of cardiac pacing pulses. These interrupts are provided via data/address bus 318. Any necessary mathematical calculations to be performed by microprocessor 324 and any updating of the values or intervals controlled by pacer timing/control circuitry 312 take place following such interrupts.

For example, in response to a sensed or paced ventricular depolarization or R-wave, the intervals separating that R-wave from the immediately preceding R-wave, paced or sensed (V-V interval) and the interval separating the paced or sensed R-wave from the preceding paced or sensed atrial depolarization (A-V interval) may be stored. Similarly, in response to the occurrence of a sensed or paced atrial depolarization (P-wave), the intervals separating that P-wave from the immediately preceding paced or sensed atrial contraction (A-A interval) and the interval separating that P-wave from the immediately preceding sensed or paced ventricular depolarization (V-A interval) may be stored.

Microprocessor 324 analyzes the stored V-V intervals and defines a desired range of A-V intervals as a function thereof. For example, the desired A-V interval range may progressively decrease as heart rates increase, in the same manner as observed in normal heart rhythm, but may be defined to include longer A-V intervals than would otherwise be observed in the patient, at similar rates. In the event that the burst stimulation function is only enabled in response to predefined rhythms, the microprocessor also optionally analyzes the stored V-V intervals to determine whether the or not the heart's rhythm meets the predetermined criteria for enabling the burst stimulation function. The desired A-V interval range in this case may similarly vary as a function of the detected rhythm, in a manner to define A-V intervals which are prolonged as compared to the patient's normally seen A-V intervals in the presence of the defined rhythm.

In the event that the burst stimulation function is enabled, microprocessor 324 also compares the observed A-V intervals to the desired interval range, to activate burst stimulation if necessary and to adjust the intensity of the burst stimulation to maintain the observed A-V intervals within the desired range. As discussed above, the burst pulses are preferably delivered during the refractory period of the chamber to which they are synchronized, and therefore are typically delivered 0–50 milliseconds following the sensed or paced depolarization.

The types of depolarizations to which the stimulus bursts are synchronized is determined by programming. In the context of the disclosed embodiment of the present invention, selection of synchronization to atrial depolarizations, normally conducted ventricular depolarizations and PVC's is provided. Typically, burst pulses will be synchronized to only one chamber of the heart.

Optionally the device may include a sensor 330 and associated sensor processing circuitry 328, which presents digitized sensor derived values of a physiologic parameter to microprocessor 324. Sensor 330 may be an oxygen sensor, as disclosed in U.S. Pat. No. 4,750,495 issued to Moore et al. on Jul. 31, 1989, a pressure transducer as disclosed in U.S. Pat. No. 4,485,813 issued to Anderson et al. on Dec. 4, 1984, a physical activity sensor as disclosed in U.S. Pat. No. 4,428,378, issued to Anderson et al on Jan. 31, 1984 or a ventricular impedance plethysmograph as disclosed in U.S. Pat. No. 4,535,774 issued to Olson on Aug. 20, 1985, all of which are incorporated herein by reference in their entireties. In the event that a physiologic sensor is employed, the output of the sensor may be employed to regulate pacing rate in a conventional fashion. In such cases, the sensor output may also be employed to define the desired A-V interval range, as an alternative to using the sensed heart rate to regulate the desired A-V interval range.

FIGS. 4A through 4D are functional flow charts illustrating the operation of the microprocessor to control the pacer circuitry 312 and the burst generator 332, in a dual chamber (DDD) pacing mode. The illustrated device may be programmed to perform several alternate burst stimulation modes, including a first mode in which the burst stimulus function is continuously activated and is employed to continuously adjust the A-V interval, a second mode in which the burst stimulus pulse function is only activated in response to a high ventricular rate, and a third mode in which the burst stimulus function is activated in response to the occurrence of premature ventricular contractions. All three alternate operational modes of the present invention may be available in the same device, selected by means of external programming control. The flowcharts of FIGS. 4A through 4D should be understood in this context.

Figure 4A:
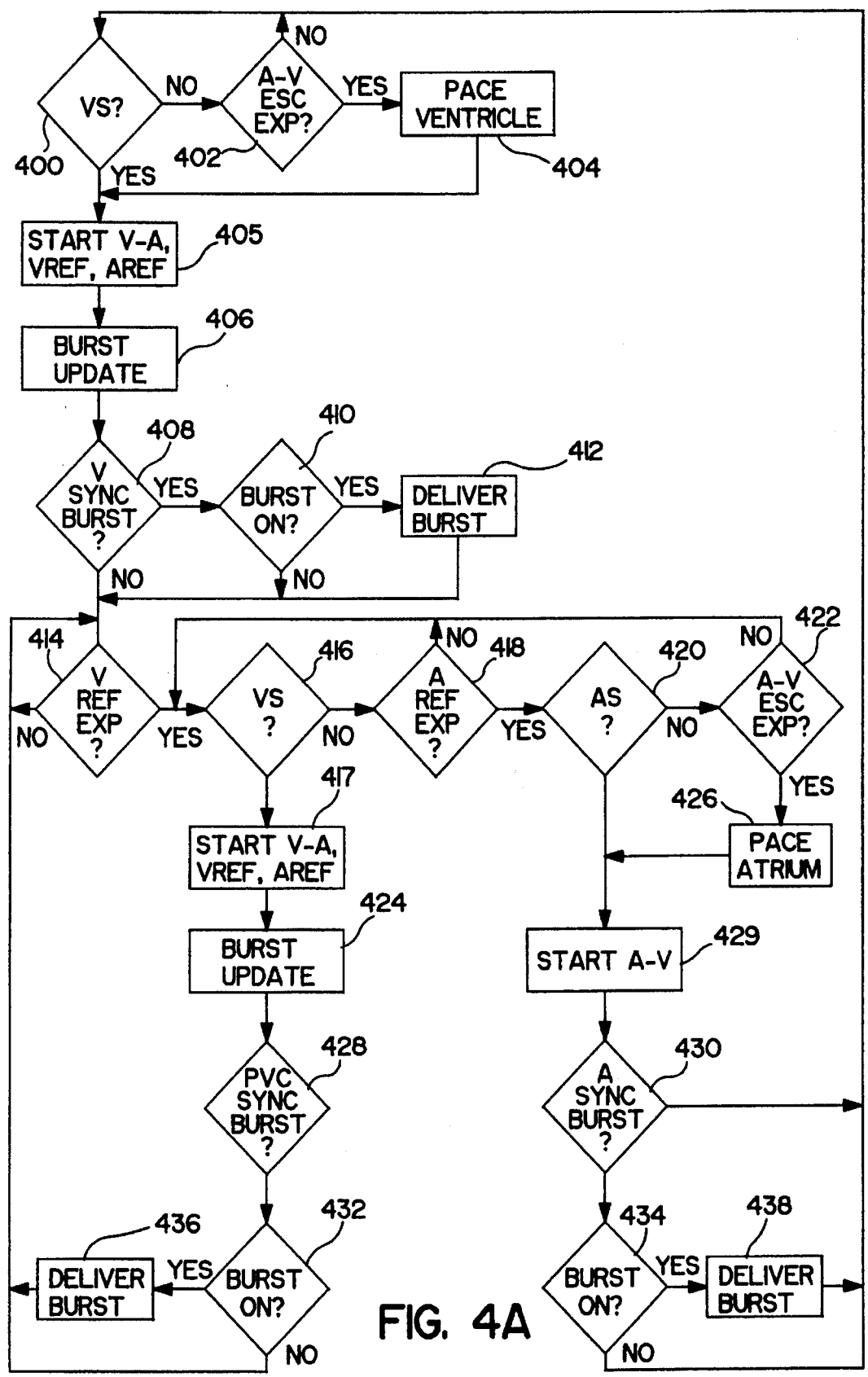
FIGS. 4A–4D are functional flow charts illustrating methods of operation of the device illustrated in FIG. 3.

FIG. 4A is a flowchart illustrating the general operation of the device, including its operation as a dual chamber pacemaker configured to operate in the DDD pacing mode, in which the atrium and ventricle are both sensed and both paced, corresponding to the pacing mode disclosed in U.S. Pat. No. 4,312,355, issued to Funke, on Jan. 26, 1982, incorporated herein by reference in its entirety. However, as noted above, the invention may also be embodied in pacemakers having other operative modes. However, it is contemplated that the invention is preferably practiced in the context of a pacemaker having the ability to sense in both the atrium and the ventricle, to allow for feedback control of the A-V interval, as altered by the burst stimulus pulses.

The flowchart may be entered at 400, at which point the pacer is timing its A-V escape interval. As such, at 400, it should be understood that the pacemaker has previously delivered an atrial pacing pulse or sensed an atrial depolarization, which initiated timing of the pacemaker's A-V escape interval, in a conventional fashion. During this time period, atrial sensing may be disabled, and, following a short blanking period, ventricular sensing is enabled. At 400 the device checks to determine whether a ventricular depolarization has been sensed during the A-V interval. If so, the ventricular and atrial refractory periods and the V-A A escape interval are initiated at 405. If a ventricular depolarization is not sensed, then at expiration of the A-V interval as detected at 402, a ventricular pacing pulse is delivered at 404 and the ventricular and atrial refractory periods and the V-A escape interval are initiated at 405. In this case, the device's A-V escape interval is employed as the observed A-V interval for purposes of updating the burst stimulus function.

Figure 4B:
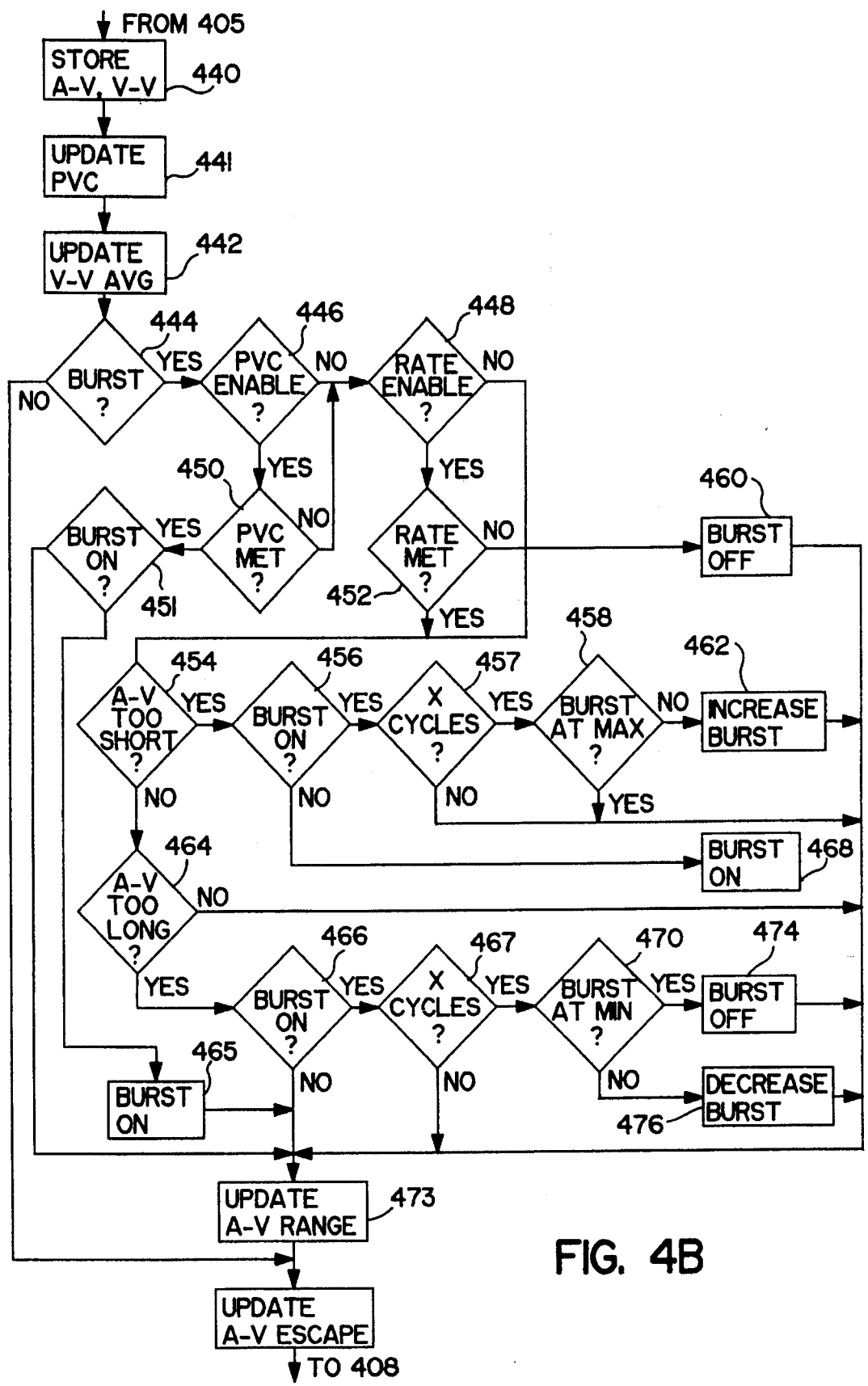

The measured A-V interval is used to update the burst stimulation function parameters at 406, to determine whether the A-V interval falls within the desired interval range, both in conjunction with enabling and activation of the AV nodal stimulus burst function and in conjunction with adjusting the intensity of the burst stimulus pulses. FIG. 4B, discussed below, discloses the burst stimulus parameter updating function of block 406 in greater detail.

At 408, the device checks to see whether it has been programmed to deliver stimulus pulses synchronized to the ventricle. If so, the device checks at 410 to determine whether the burst stimulus function has been activated, and if so, a synchronized stimulus burst is delivered at 412 according to the parameters defined during the stimulus pulse update function at 406. The device then checks at 414 to determine whether the ventricular refractory period following delivery of a pacing pulse at 404 or sensing of a ventricular depolarization at 400 has expired. Similarly, if the burst function is found not to be activated at 410, the device awaits expiration of the ventricular refractory period at 414.

Following expiration of the ventricular refractory period, the device attempts to determine at 416 whether a ventricular depolarization is sensed during the V-A escape interval at 416. If not, the device checks at 418 to determine whether the atrial refractory period, initiated on ventricular sensing at 400 or ventricular pacing at 404 has expired. If so, the device checks at 420 to determine whether an atrial event is sensed during the V-A escape interval. The device continues to look for sensed atrial and ventricular depolarizations until expiration of the V-A escape interval at 422.

If a ventricular depolarization is sensed at 416, during the V-A interval, it is diagnosed as a premature ventricular contraction, re-initiating the ventricular and atrial refractory periods and the V-A escape interval at 417 and initiating the burst parameter update function at 424. The burst parameter update function at 424 corresponds exactly to the burst parameter update function at 406. At 428 the device checks to determine whether it has been programmed to deliver stimulus pulse bursts synchronized to PVC's. If not, the device simply returns to block 414, awaiting expiration of the ventricular refractory period. If PVC synchronized bursts are programmed, the device checks at 432 to determine whether the burst function has been activated. If so, a burst is delivered at 436, synchronized to the PVC sensed at 416, and falling within the ventricular refractory period. If not, the device simply returns to block 414, awaiting expiration of the ventricular refractory period.

If time-out of the V-A interval occurs at 422 without atrial or ventricular sensing, an atrial pacing pulse is generated at 426. In the event that an atrial depolarization is sensed at 420, during the V-A interval, or following generation of an atrial pacing pulse,the A-A interval may optionally be measured and stored. The A-V escape interval is then initiated at 429 and the device checks at 430 to determine whether it has been programmed to deliver stimulus bursts synchronized to atrial depolarizations. If not, the device returns to 400, awaiting ventricular sensing or expiration of the A-V interval. If atrial synchronized bursts have been programmed the device checks at 434 to determine whether the burst stimulus function has been activated. If so, a stimulus burst synchronized to the sensed or paced atrial depolarization at 420 is delivered in the refractory period of the atrium, and the device awaits time out of the A-V interval or ventricular sensing at 400. If the burst stimulus function has not been activated, the device simply returns directly to 400 to await ventricular sensing or a time oun of the A-V interval.

FIG. 4B illustrates the burst stimulus update function performed in block 406, in FIG. 4A. The stimulus burst update function is entered from block 405, following initiation of the V-A interval. The measured V-V and A-V intervals are stored at 440 and at 442, the stored V-V interval is employed to update the V-V average. At 444, the device checks to determine whether it has been programmed to allow enablement of the AV nodal fat pad stimulation function. If not, the device optionally updates the A-V escape interval at 472 as a function of average rate and awaits expiration of the ventricular refractory period at 414. Alternatively, if a sensor is employed, the A-V interval and/or the pacing rate may be updated as a function of the sensor output.

In the event that burst stimulation is been allowed by programming, the device checks at 446 to determine whether the device has been programmed to enable AV nodal fat pad stimulation in response to the occurrence of premature ventricular contractions. If so, the device checks at 450 to determine whether the criterion for enabling the burst stimulation function has been met. For example, the criterion may be considered to be met in response to four of the preceding eight ventricle depolarizations having been PVC's, or in response to the one or two immediately preceding ventricular depolarizations having been PVC's. The specific criterion employed may be programmable by the physician. In the event that the PVC criterion is met at 450, the device checks at 451 to determine whether the burst function is activated. If not, the burst stimulus function is activated at 465 and the A-V range and A-V escape intervals are updated at 473 and 475.

In the event that either PVC enabled burst stimulation is not programmed or in the event that PVC based criterion for enabling burst stimulation is not met at 450, the device checks at 448 to determine whether it has been programmed to enable burst stimulation in response to a detected high heart rate. If so, the device checks at 452 to determine whether the V-V interval average calculated at 442 meets a programmed rate. Alternatively, if a physiologic sensor is employed, enablement of the burst stimulus function may occur in response to the output of the sensor meeting predetermined criteria, suggesting the need for increased cardiac output or suggesting the presence of reduced cardiac output.

In the event that enablement of the burst stimulation function based on high rate is programmed and the criterion is not met, the burst function is deactivated at 450. In the event that the rate based criterion is met, or in the event that fat pad stimulation is not subject to a rate based criterion for enablement, the device checks at 454 to determine whether the immediately preceding observed A-V intervals have is less than the minimum value of the desired A-V interval range. If so, the device checks at 456 to determine whether the burst stimulus function was previously activated. If not, the burst function is activated at 468 and a burst will be delivered synchronized to the next subsequent atrial or ventricular depolarization, according to device programming, at an initial stimulus intensity programmed by the physician.

In the event that the burst function was previously activated, and the A-V interval observed is still too short, the device checks at 457 to determine whether a minimum number "X" of stimulus pulse bursts have been delivered since activation of burst stimulation or adjustment of stimulus parameters. If so, the device checks at 458 to determine whether the parameters for the stimulus burst are at their maximum available intensity. If not, the intensity of subsequent fat stimulus bursts is increased at 462. If the intensity is already at the maximum level, or if the minimum number of bursts have not been delivered, no adjustment is made to the stimulation intensity. Changes in stimulation intensity should be limited for each adjustment to avoid over-shooting the desired stimulation parameters. A physician programmed fixed increment in the parameter or parameters to be varied, based on testing of the device as implanted is thus desirable.

If the observed A-V interval is not too short, the device checks at 464 to determine whether the observed A-V interval exceeds the upper limit of the desired interval range. This situation may be indicated by delivery of a ventricular pacing pulse at the expiration of the pacemaker's A-V escape interval. If not, the observed A-V is determined to have fallen within the desired interval range, and no adjustment is made to the burst stimulus function. If the burst stimulus function is not activated, it remains inactivated. If the burst stimulus function is activated, it remains activated at its present parameters.

In the event that the observed A-V interval is too long, the device checks at 466 to determine whether the burst stimulation function is activated. If so, the device checks at 467 to determine whether a minimum number "Y" of stimulus pulse bursts have been delivered since activation of burst stimulation or adjustment of stimulus parameters. "X" may be the same as or different from "Y". If the minimum number has not been delivered, no adjustment is made. If the minimum number has been delivered, the device checks at 470 to determine whether the parameters of the stimulus bursts are at the minimum values. If not, the intensity of the burst is decreased at 476. If so, the burst function is simply inactivated at 474.

After adjustment, activation or deactivation of the burst stimulus function, the device updates the desired range of A-V intervals at 473 as a function of the preceding sensed heart rhythm. The desired A-V interval duration and range may be defined as a function of the average heart rate over the preceding series of beats. Alternatively, if a sensor is employed, the A-V interval range may be updated as a function of the sensor output. At 472, the A-V interval is updated, as discussed above. If burst stimulation is enabled, the pacemaker's A-V escape interval is set to equal or exceed the maximum A-V interval duration of the desired A-V interval range. The device then returns to 408 to determine whether a synchronized burst has been scheduled, with further operation of the device as discussed above.

The flow chart of FIG. 4B is based on the premise that termination of burst stimulation will generally occur as a function of the observed effects on the A-V interval or in response to the cessation of the heart rhythm (e.g. high rate or PVC's) which enabled the burst stimulus function. However, it is also within the scope of the present invention to limit the pulse bursts to a maximum number (one or more) of stimulus bursts each time the function is activated. This feature would be most desirable in the context of stimulus bursts intended to prevent or terminate arrhythmias.

Figure 4C:
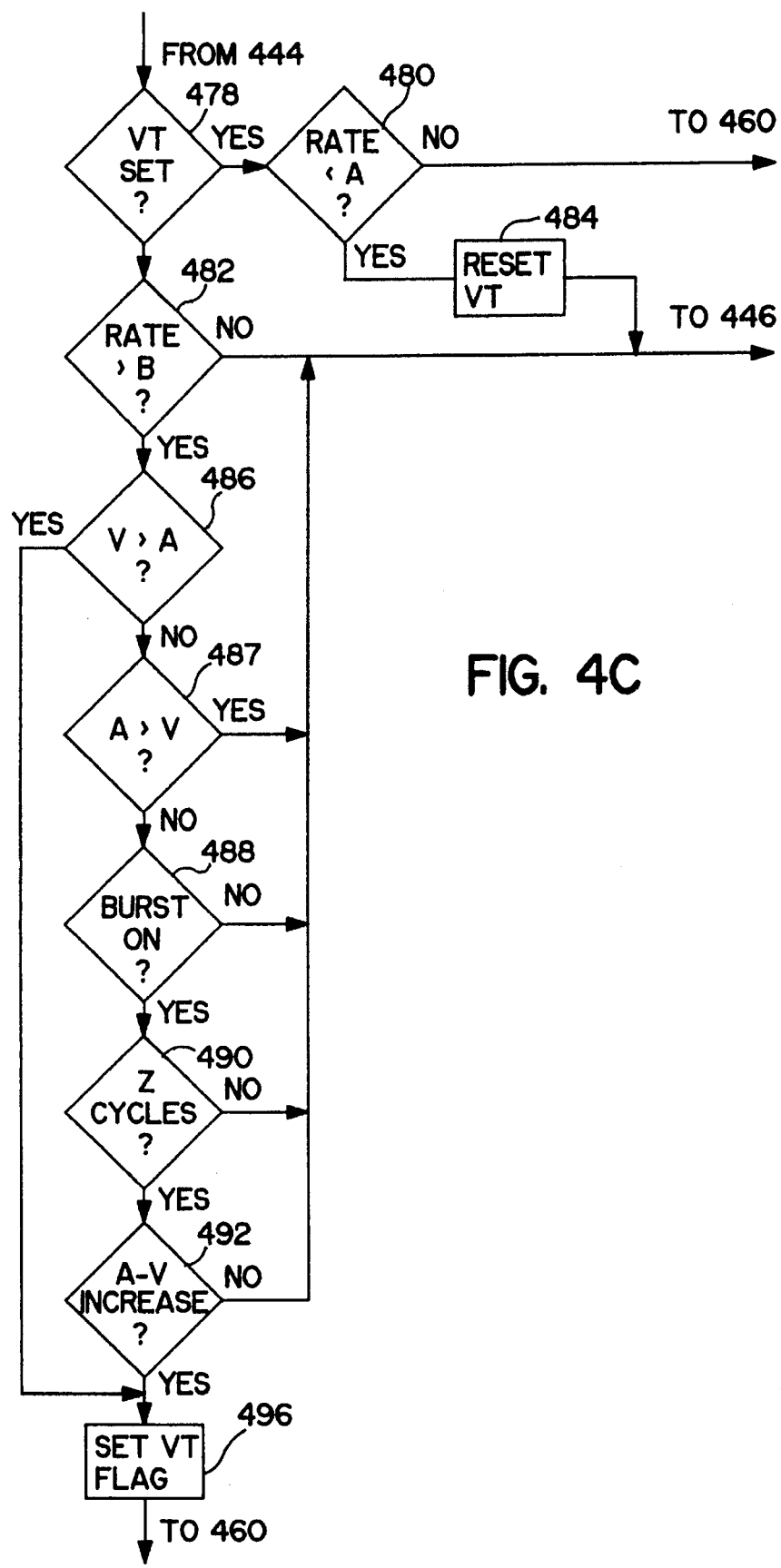
Figure 4D:
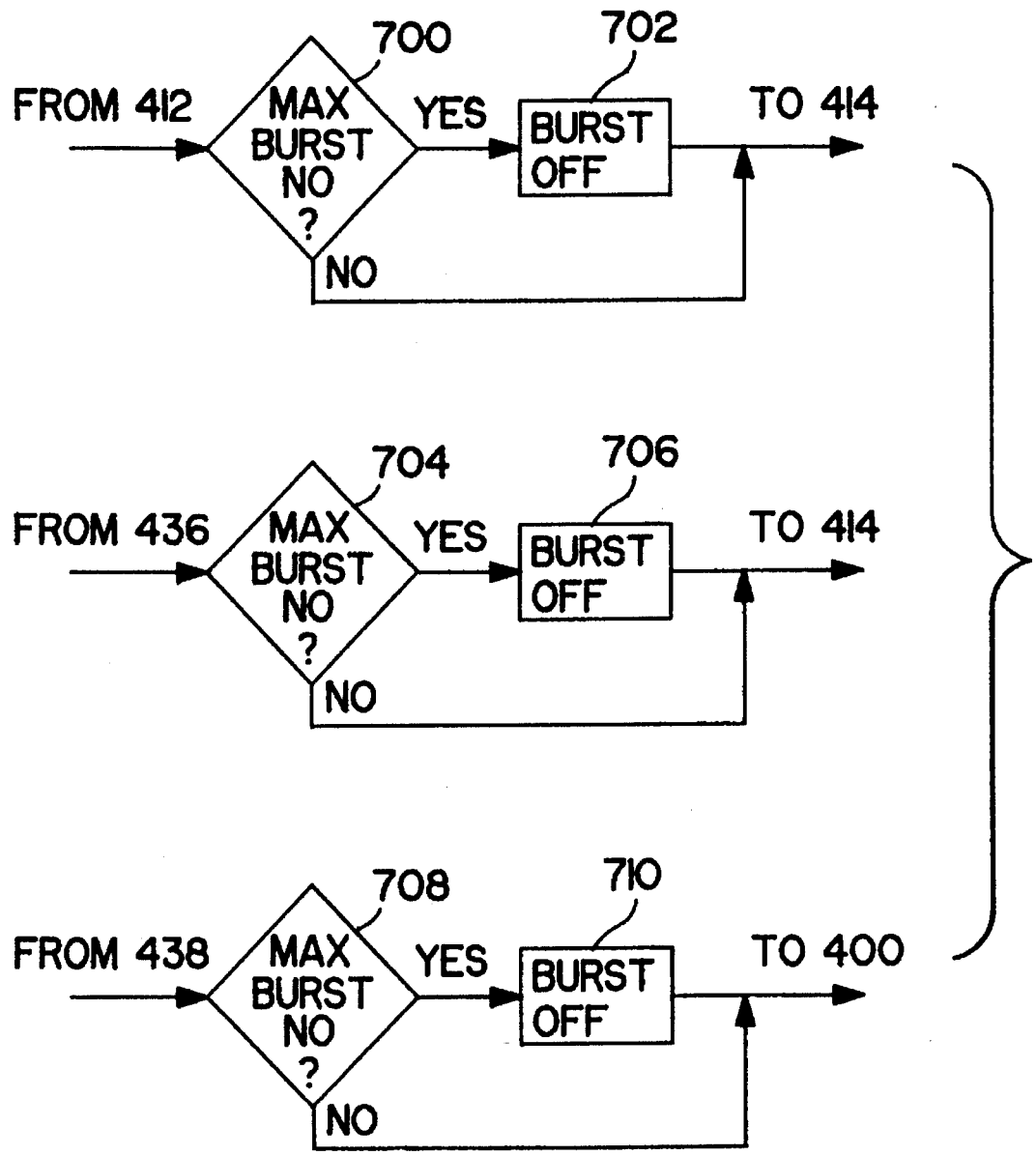

If a limit on the number of bursts provided is desired, some or all of the supplemental functions illustrated in FIG. 4D should be added to the flow chart of FIG. 4A, to be performed after pulse burst deliveries. In this case, after delivery of a pulse burst at 412, 436 or 438, the device checks at 700, 704 or 708, respectively, to determine whether a maximum number of pulse bursts has been specified and whether that number has been delivered since the burst function was most recently activated. If so, the burst function is terminated at 702, 706 or 710, and bursts will not be delivered until the next time the burst stimulus function is activated. If not, then the device will continue to deliver pulse bursts until the burst stimulus function is deactivated in response to observed A-V interval durations or by cessation of the specified heart rhythm which enabled the burst function. The number of bursts allowed may vary as a function of the activation criterion. For example, only one or two bursts may be allowable following activation of the burst stimulus function based on rate or PVC's, while there may be a substantially higher or unlimited number of allowable pulse bursts when burst stimulation is activated based on observed A-V intervals alone.

FIG. 4C illustrates how the AV nodal fat pad stimulus function, synchronized to ventricular depolarizations, may be employed to distinguish between ventricular and supraventricular tachycardia, both for diagnostic purposes and for purposes of controlling the delivery of AV nodal fat pad stimulus pulses. Rather than going directly from block 444 in FIG. 4B to block 446, the device instead first checks at 478 to determine whether a VT flag indicating the presence of a ventricular tachycardia has been set. In the event that the flag has been set, the device checks at 480 to determine whether the present heart rate is less than a preset rate "A", indicating termination of the ventricular tachycardia. If not, the device proceeds to block 460, deactivating the burst stimulation function, to avoid delivery of burst stimulus pulses in the presence of sustained ventricular tachycardia. In the event that the rate has decreased below the predefined rate "A" the VT flag is reset at 484, allowing for subsequent activation of the AV nodal stimulus function, if otherwise appropriate.

In the event that the VT flag has not been set, the device checks at 482 to determine whether the ventricular rate exceeds a specified tachycardia detection rate "B" which is preferably less than "A", and may be the same or greater than the rate employed for rate based activation of the burst stimulus function, if employed. If the VT flag is not set, the device simply returns to 446 (FIG. 4B). If the rate is greater than "B" the device checks at 486 to determine whether the preceding rhythm has exhibited higher ventricular rate than atrial rate, based on stored A-A and V-V intervals. If the heart rhythm exhibits a greater ventricular rate, it is classified as a ventricular tachycardia at 496, the VT flag is set and burst stimulation is deactivated at 460 (FIG. 4B).

If the ventricular rate is not higher than the atrial rate, the device checks at 487 to determine whether the atrial rate is higher than the ventricular rate. If so, the tachycardia is diagnosed as supraventricular and the device returns to 446 (FIG. 4b). If the atrial and ventricular rates are the same, the device checks at 488 to determine whether the burst stimulus function is activated. If so, the device checks at 490 to determine whether a minimum number of pulse bursts have been delivered since the criterion for activation of the burst function was met. If so, the device checks at 492 to determine whether the A-V interval has been shortened following activation of burst stimulation, which would indicate that the rapid rate originates in the ventricle and is conducted retrograde to the atrium. If so, the VT flag is set and burst stimulation is terminated at 460 (FIG. 4B). Otherwise, the device proceeds to block 466 (FIG. 4B), and the normal procedure for adjusting, activating or de-activating the AV nodal stimulus function as illustrated in FIG. 4B proceeds.

While the above invention is disclosed in the context of a microprocessor based architecture, the operation of the device is simple enough that it may also be implemented by means of a full custom digital integrated circuit architecture, or even a circuit architecture employing analog timing circuitry. Therefore, the above disclosure should be considered exemplary, rather than limiting with regard to the claims that follow.

In conjunction with the above disclosure, I claim:

1. An electrical medical stimulator, comprising:

electrode means for delivery of electrical stimulation to the fat pad associated with the AV node of a human heart;

pulse generator means for generating stimulus pulses and for providing said stimulus pulses to said first electrode means;

means for sensing occurrences of PVCs; and means for activating said pulse generator in response to occurrences of PVCs to deliver stimulus pulses to said electrode means, synchronized to said PVCs.

2. An electrical medical stimulator according to claim 1, wherein said activating means ccomprises means for limiting thenumber of said stimulus pulses delivered following activation of said pulse generator means in response to the occurrence of said PVC's.

3. A method of stimulating a patient's heart, comprising; sensing occurrence of PVCs in said patient's heart; and in response to occurrences of PVCs, delivering stimulus pulses to said patient's AV nodal fat pad, synchronized to said PVCs.

4. A method according to claim 3 wherein said step of sensing occurrences of PVCs comprises sensing occurrences of a predetermined number of PVCs, over a preceding series of heart depolarizations.

\* \* \* \* \*